US006748269B2

(12) United States Patent
Thompson et al.

(10) Patent No.: US 6,748,269 B2
(45) Date of Patent: Jun. 8, 2004

(54) ALGORITHM FOR DISCRIMINATION OF 1:1 TACHYCARDIAS

(75) Inventors: Julie Thompson, White Bear Lake, MN (US); Eric G. Lovett, Roseville, MN (US); Janice Jenkins, Chicago, IL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 136 days.

(21) Appl. No.: 09/982,116

(22) Filed: Oct. 17, 2001

(65) Prior Publication Data

US 2003/0074026 A1 Apr. 17, 2003

(51) Int. Cl.$^7$ ............................. A61N 1/39; A61N 1/36
(52) U.S. Cl. ........................... 607/4; 600/515; 600/518
(58) Field of Search ................ 600/515, 516, 600/518; 607/4, 5, 9, 25

(56) References Cited

U.S. PATENT DOCUMENTS

| | | | |
|---|---|---|---|
| 4,583,553 A | 4/1986 | Shah et al. ................ 128/704 |
| 5,002,052 A | 3/1991 | Haluska ................ 128/419 PG |
| 5,183,040 A | 2/1993 | Nappholz et al. ..... 128/419 PG |
| 5,184,615 A | 2/1993 | Nappholz et al. ..... 128/419 PB |
| 5,193,535 A | 3/1993 | Bardy et al. ............ 128/419 D |
| 5,203,326 A | 4/1993 | Collins ................ 128/419 PG |
| 5,205,283 A | * 4/1993 | Olson ............................ 607/4 |
| 5,217,021 A | 6/1993 | Steinhaus et al. ........... 128/702 |
| 5,251,621 A | 10/1993 | Collins .......................... 607/4 |
| 5,257,621 A | 11/1993 | Bardy et al. ................... 607/5 |
| 5,311,874 A | 5/1994 | Baumann et al. ........... 128/705 |
| 5,327,900 A | * 7/1994 | Mason et al. ................ 600/518 |
| 5,379,776 A | * 1/1995 | Murphy et al. ............. 600/518 |
| 5,383,910 A | * 1/1995 | den Dulk ..................... 607/14 |
| 5,713,932 A | * 2/1998 | Gillberg et al. .............. 607/27 |
| 5,730,141 A | 3/1998 | Fain et al. ................... 128/705 |
| 5,776,072 A | 7/1998 | Hsu et al. .................... 600/518 |
| 5,836,975 A | 11/1998 | DeGroot ........................ 607/5 |
| 5,836,976 A | 11/1998 | Min et al. ...................... 607/6 |
| 5,868,793 A | 2/1999 | Nitzsche et al. ............... 607/5 |
| 5,873,897 A | 2/1999 | Armstrong et al. ........... 607/14 |
| 5,882,352 A | 3/1999 | Duncan et al. ................. 607/4 |
| 5,891,043 A | 4/1999 | Ericksen et al. ............. 600/508 |
| 5,891,170 A | 4/1999 | Nitzsche et al. ............... 607/4 |
| 5,893,882 A | 4/1999 | Peterson et al. .............. 607/14 |
| 5,954,752 A | 9/1999 | Mongeon et al. .............. 607/6 |
| 5,968,079 A | 10/1999 | Warman et al. ................ 607/5 |
| 5,978,700 A | 11/1999 | Nigam ......................... 600/518 |
| 5,978,707 A | 11/1999 | Krig et al. .................... 607/14 |
| 5,987,356 A | 11/1999 | DeGroot ........................ 607/5 |
| 6,007,493 A | 12/1999 | Ericksen et al. ............. 600/508 |
| 6,456,871 B1 | 9/2002 | Hsu et al. .................... 600/518 |

FOREIGN PATENT DOCUMENTS

EP 0617980 10/1994 .......... A61N/1/368

OTHER PUBLICATIONS

Lecarpentier, G L., et al., "Differentiation of sinus tachycardia from ventricular tachycardia with 1:1 ventriculoatrial conduction in dual chamber implantable cardioverter defibrillators: feasibility of a criterion based on the artrioventricular interval", *Pacing Clin Electrophysiol., 17(11 Pt 1)*, (Nov. 1994), 1818–31.

Nair, M , et al., "Automatic arrhythmia identification using analysis of the atrioventricular association. Application to a new generation of implantable defibrillators. Participating Centers of the Automatic Recognition of Arrhythmia Study Group.", *Circulation, 95(4)*, (Feb. 1997), 967–73.

(List continued on next page.)

*Primary Examiner*—Carl Layno
(74) *Attorney, Agent, or Firm*—Schwegman, Lundberg, Woessner & Kluth, P.A.

(57) ABSTRACT

An algorithm for detection of tachycardias and for discriminating between supraventricular tachycardia (SVT) and ventricular tachycardia (VT) when a 1:1 tachycardia condition is present that can be implemented in an implantable cardiac rhythm management device. Variability measures of AV and VA intervals during the tachycardia are computed and used to distinguish between SVT and VT.

26 Claims, 3 Drawing Sheets-

OTHER PUBLICATIONS

Stevenson, S A., et al., "A:V=1:1 cardiac arrhythmia detection by VA interval analysis", *J Electrocardiol., 29 Suppl,* (1996), 198–201.

Thompson, Julie A., "An Improved Method of Discriminationof 1:1 Tachycardias using a Variance Based Model of Electrical Conduction of the Heart", *Ph.D. Dissertation, University of Michigan,* (2000), 194.

Thompson, Julie , et al., "Improved Differentiation of 1:1 Tachycardias in Dual–Chamber ICDs Using Interval Variability", *Noth American Society of Pacing and Electrophysiology (NASPE) Conference held in Boston, MA on May 4, 2001.,* 14.

Thompson, J , et al., "Recognition of ventricular tachycardia with 1:1 retrograde atrial activation: A new algorithm for implantable cardioverter defibrillators", *Proceedings of the 19th Annual International Conference of the IEEE Engineering in Medicine and Biology Society. 'Magnificent Milestones and Emerging Opportunities in Medical Engineering', pt. 1, vol. 1,* (1997),393–4.

Thompson, J A., et al., "Ventriculoatrial conduction metrics for classification of ventricular tachycardia with 1:1 retrograde conduction in dual–chamber sensing implantable cardioverter defibrillators", *J Electrocardiol., 31 Suppl,* (1998), 152–6.

Throne, R D., et al., "Discrimination of retrograde from anterograde atrial activation using intracardiac electrogram waveform analysis", *Pacing Clin Electrophysiol., 12(10),* (Oct. 1989), 1622–30.

\* cited by examiner

//—

ALGORITHM FOR DISCRIMINATION OF 1:1 TACHYCARDIAS

FIELD OF THE INVENTION

This invention pertains to methods and systems for treating cardiac arrhythmias. In particular, it deals with discriminating between different types of tachyarrhythmias.

BACKGROUND

Tachyarrhythmias are abnormal heart rhythms characterized by a rapid rate, typically expressed in units of beats per minute (bpm), that can originate in either the ventricles or the atria. Examples of tachyarrhythmias include sinus tachycardia, atrial tachycardia, atrial fibrillation, ventricular tachycardia, and ventricular fibrillation. The most dangerous tachyarrythmias are those that have their origin in the ventricles, namely ventricular tachycardia (VT) and ventricular fibrillation (VF). Ventricular rhythms occur when re-entry of a depolarizing wavefront in areas of the ventricular myocardium with different conduction characteristics becomes self-sustaining or when an excitatory focus in the ventricle usurps control of the heart rate from the normal physiological pacemaker of the heart, the sino-atrial node. The result is rapid contraction of the ventricles out of electromechanical synchrony with the atria. Most ventricular rhythms exhibit an abnormal QRS complex in an electrocardiogram (ECG) because they do not use the specialized conduction system of the ventricles, the depolarization spreading instead from the excitatory focus or point of re-entry directly into the myocardium. In ventricular tachycardia, the ventricles contract rapidly and produce distorted QRS complexes in an ECG. Ventricular fibrillation, on the other hand, occurs when the ventricles depolarize at an even more rapid rate and in a chaotic fashion, resulting in QRS complexes of constantly changing shape and virtually no effective pumping action. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardiac rhythm management devices known as implantable cardioverter/defibrillators (ICDs) are designed to treat ventricular tachyarrhythmias by delivering an electrical shock pulse to the heart. Cardioversion and/or defibrillation can be used to terminate most tachyarrhythmias, including VT and VF. The electric shock terminates the tachyarrhythmia by depolarizing all of the myocardium simultaneously and rendering it refractory.

Another type of electrical therapy for tachycardia is antitachycardia pacing (ATP). In ATP, the heart is competitively paced with one or more pacing pulses in an effort to interrupt the reentrant circuit causing the tachycardia. ATP therapy can successfully treat VT, but it is not effective in terminating VF. Modem ICDs incorporate ATP capability so that ATP therapy can be delivered to the heart when a tachycardia is detected. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible.

In most ICDs with ATP capability, VF is distinguished from VT using rate-based criteria so that ATP or shock therapy can be delivered as appropriate. The heart rate is usually determined by measurement of the time interval between successive ventricular depolarizations. A measured heart rate is classified as a tachycardia when the rate is in a VT zone, defined as a range of rates above a tachycardia detection rate (TDR) but below a fibrillation detection rate (FDR). A measured heart rate above the FDR, on the other hand, is in the VF zone and is classified as fibrillation. In a typical device, a tachyarrhythmia with a heart rate in the VT zone is treated with ATP therapy in order to avoid an unnecessary painful shock to the patient, and a defibrillation shock is delivered if the heart rate is in the VF zone or if ATP pacing fails to terminate a tachyarrhythmia in the VT zone.

As aforesaid, VT can be detected when the ventricular rate falls within the VT zone. A rapid ventricular rate in the VT zone, however, is not necessarily due to VT but can also result from a tachyarrhythmia that originates from above the ventricles. Such tachyarrhythmias are referred to as supraventricular tachycardias (SVT's) and include sinus tachycardia, atrial tachycardia, and atrial fibrillation. The normal rhythmic impulse of the heart is first generated in pacemaker tissue known as the sino-atrial (SA) node, spreads throughout the atria causing atrial contraction, and is then conducted to the atrioventricular (AV) node where the impulse is delayed before passing into the ventricles. The ventricles of a normal heart are then electrically stimulated by excitation emanating from the AV node that spreads via specialized conduction pathways. An abnormal rhythm in the atria can thus be transmitted antegradely to the ventricles in patient whose AV conduction pathway is intact. Such an SVT is characterized by elevated rates in both the atria and the ventricles. Elevated rates in both the atria and ventricles can also occur with VT as well, however, due to retrograde conduction of excitation from the ventricles to the atria. Such retrograde conduction is possible in most people and confounds the discrimination between VT and SVT based upon atrial and ventricular rates alone when both rates are similar, a condition known as a one-to-one or 1:1 tachycardia.

It is desirable for an ICD to differentiate between an SVT and a VT, however, both for reasons of efficacy and safety. ATP therapy delivered to treat an SVT will not be effective and potentially could make matters worse by triggering a ventricular arrhythmia. Also, although most ICD's currently on the market today are designed to treat only tachyarrhythmias of ventricular origin, some newer designs are capable of treating atrial tachyarrhythmias as well. It is thus important for an ICD to recognize that an elevated ventricular rate is due to an SVT rather than a VT so that either ventricular ATP therapy can be withheld or more appropriate therapy can be delivered. Conversely, because VT is generally a more serious condition, the ICD also needs to detect VT with a high degree of sensitivity so that therapy can be delivered promptly.

SUMMARY OF THE INVENTION

The present invention relates to an algorithm that can be implemented in a cardiac rhythm management device for tachycardia detection and for discriminating between a ventricular tachycardia and a supraventricular tachycardia when both the atrial and ventricular rates are elevated and within defined tachycardia ranges. The device detects tachycardias by detecting atrial and ventricular senses corresponding to atrial and ventricular depolarizations, respectively, and measuring the cycle length between consecutive senses in each chamber. An AA interval corresponding to a cycle length between consecutive atrial senses, and a VV interval corresponding to a cycle length between consecutive ventricular senses, are both computed, preferably as a median or other statistic of a number of individual cycle lengths measured during a data collection time window. Ventricular fibrillation (VF) is then detected when the VV interval is below a VF threshold. If the VV interval is within a tachycardia range defined as above the VF threshold but below a VT threshold, and the AA interval is within normal limits, a ventricular tachycardia (VT) is detected. If the AA interval is within a tachycardia range defined as below an SVT threshold, and the VV interval is within normal limits, a supraventricular tachycardia (SVT) is detected. A dual tachycardia is detected if the VV and AA intervals are both within their respective tachycardia ranges and differ by more than a specified dual tachycardia limit value. A dual tachycardia refers to condition in which both VT and SVT are present simultaneously. A dual tachycardia is presumed when the atrial and ventricular rates are so different from one another that the atria and ventricles can be assumed to be independently driven. Since VT is the more serious condition, a dual tachycardia can be regarded as a VT for treatment purposes.

If a 1:1 tachycardia condition is present, defined as when the AA and VV intervals are both within their tachycardia ranges and differ from one another by no more than some specified 1:1 limit value (e.g., a percentage or an absolute rate difference), the tachycardia may be either an SVT or a VT. To distinguish between these possibilities, an interval variability measure is employed. AV intervals corresponding to a cycle length between an atrial sense and a next occurring ventricular sense with no intervening atrial sense, and VA intervals corresponding to a cycle length between a ventricular sense and a next occurring atrial sense with no intervening ventricular sense are both collected during a time window. Variabilities are then computed for both the VA and AV intervals based upon their measured individual cycle lengths during a specified time window, where the variability measure is preferably an average deviation calculated as the sum of the absolute value of the difference of each cycle length from the mean divided by the number of cycle lengths in the time window. Other alternatives for the variability measure include the variance of the cycle lengths measured during the specified time window, the difference between the maximum and minimum cycle lengths measured during the specified time window after the exclusion of outlier values, a difference between an upper percentile value and a lower percentile value of the cycle lengths measured during the specified time window after the exclusion of outlier values, and a sum of consecutive cycle length differences measured during the time window.

SVTs and VTs are then distinguished based upon the relative variability of the VA and AV intervals. The algorithm discriminates between an SVT and a VT when a 1:1 tachycardia condition is present by detecting an SVT if the VA interval variability exceeds the AV interval variability and detecting a VT if the AV interval variability exceeds the VA interval variability. A refinement to the algorithm comes from recognizing that one particular type of SVT, atrioventricular nodal reentrant tachycardia (AVNRT) is characterized by near simultaneous excitation of the atria and ventricles. Accordingly, when a 1:1 tachycardia condition is present and when either the AV or VA interval is less than a specified AVNRT limit value (e.g., 80 milliseconds), AVNRT may be detected regardless of the AV and VA interval variabilities.

The algorithm may be further refined to take advantage of the predictive value of the relative magnitudes of the AV and VA intervals during lower rate 1:1 tachycardias. The AV and VV intervals may each be represented by a median or other statistic of a number of individual cycle lengths measured during the data collection time window. Then, if the VV interval is no is more than a specified ratebreak threshold value during a 1:1 tachycardia, an SVT may be distinguished from a VT by detecting an SVT if the VA interval exceeds the AV interval and detecting a VT if the AV interval exceeds the VA interval, irrespective of the AV and VA interval variabilities. Relative VA and AV interval magnitudes cannot be reliably used to distinguish SVT from VT in patients with first degree AV block, however, owing to their slowed AV conduction velocities. The algorithm may therefore be further modified to not employ relative VA and AV interval magnitudes for VT/SVT discrimination in patients known to have first degree AV block. In such patients, however, an additional criterion may employed that supercedes discrimination on the basis of relative AV and VA interval variability: a VT is detected if a measured AV conduction time in the patient during a normal rhythm is less than a specified AV block limit value and the AV interval during a tachycardia is greater than a specified tachycardia AV limit value. Exemplary values for the specified AV block limit value and the specified tachycardia limit value are 270 and 300 milliseconds, respectively.

DETAILED DESCRIPTION

For the reasons stated above, accurate discrimination of 1:1 tachycardias would be a very useful capability for an ICD. Much of the previous research that has been done in this area has relied on signal morphology to distinguish between SVTs and VTs where the morphologies of the individual electrogram waveforms are analyzed. Morphology based methods have shown promise, but these methods require computational complexity that may be beyond the capability a small battery powered device such as an ICD. The present invention, on the other hand, is a computationally efficient method for discrimination of 1:1 tachycardias that is relies upon the relative variability of measurable intervals that may be readily implemented in an ICD. In what follows, the algorithm will be described in detail and its physiological basis explained.

1. Physiological Basis

Figure 1:
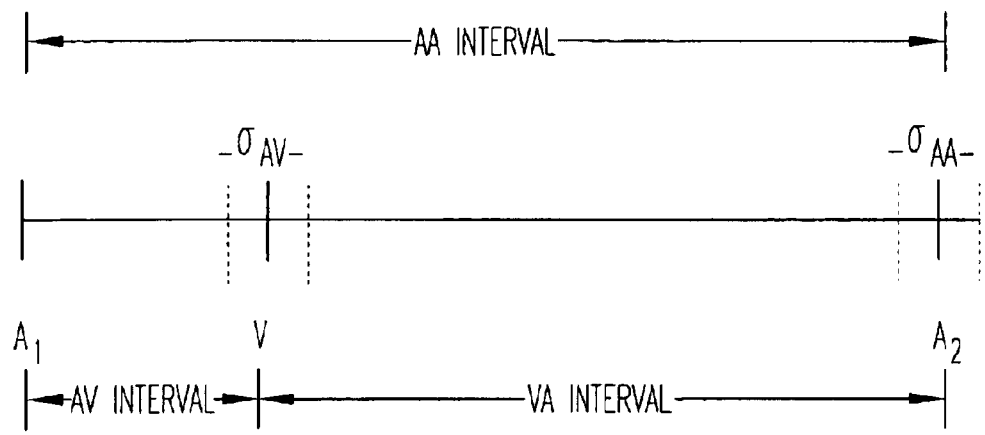
FIG. 1 is a timing diagram of a supraventricular rhythm.

In normal sinus rhythm, which is a supraventricular rhythm, the electrical impulse begins from spontaneous depolarization in the sinoatrial (SA) node. This impulse propagates through the atria to the atrioventricular (AV) node. The AV node introduces a delay, then the depolarization signal continues down to activate the ventricles. The timing of this process is a function of the speed of signal propagation through the atrial tissue, AV node, and ventricles, and the distance of signal transmission in each region. This conduction pattern repeats indefinitely. The timing as measured from atrial depolarization to the subsequent ventricular depolarization, denoted the AV interval, is relatively consistent from one beat to the next, but does reflect a certain amount of natural variance. This process is repeated at the initiation of the next atrial impulse. The timing between successive atrial depolarizations is determined by the intracellular activity of ionic currents, and is also subject to some variability, called the AA interval variance. The VA interval of a normal cycle, then, is the time measured from ventricular depolarization to the next atrial impulse. There is no direct physical relationship between this ventricular impulse and the next atrial impulse. The earlier ventricular impulse was determined by the previous atrial impulse, and the next atrial impulse is determined by the electrochemical activity in the sinus node. So the VA interval can safely be viewed as merely the subtraction of the AV interval from the VA interval—the remainder of the AA cycle. FIG. 1 shows a timing diagram for a supraventricular rhythm illustrating these relationships. The variability of the AV interval over several successive cycles can be measured with a variance calculation and noted as $\sigma^2_{AV}$ where AV is the random variable representing the AV intervals. The variance of the AA interval over several cycles can likewise be calculated, designated as $\sigma^2_{AA}$. The VA interval (merely a mathematical derivation of the AV and AA intervals) has a variance imposed upon it which is a function of the AV variance and the AA variance. Since the AV interval is determined solely by atrioventricular conduction characteristics, and the AA interval is determined by the electrochemical processes responsible for automaticity in the cells of the SA node, these two factors are assumed to be independent. The VA variance $\sigma^2_{VA}$ is thus calculated as:

$$\sigma^2_{VA} = \sigma^2_{AA} + \rho^2_{AV}$$

While the AV variance has a value of $\sigma^2_{AV}$ and the AA variance a value of $\sigma^2_{AA}$, the VA variance has a value of $\sigma^2_{AV} + \sigma^2_{AA}$ which thus is larger than either $\sigma^2_{AV}$ or $\sigma^2_{AA}$ (assuming neither of these quantities is zero). Thus, in a supraventricular arrhythmia the VA variance will be larger than the AV variance.

In a ventricular tachycardia conducting retrogradely through the AV node and depolarizing the atrium the reverse situation exists. The VA interval represents the time interval from ventricular depolarization backwards through the AV node to atrial conduction. This sequence has a VA variability associated with it similar to the AV variance in the antegrade case. The ventricular chamber is now controlling the heart activity so the ventricular to ventricular cycle (VV) is the driving force and has a VV interval variability governed by the arrhythmia mechanism on the cellular level. In this situation the AV interval is merely the remainder of the cycle from atrial depolarization to the next ventricular depolarization and does not directly represent a physiological event. A similar analysis can be done for the retrograde situation as was previously shown for an antegrade situation. This time the relevant random variables are VA and VV, and the variances associated with them are $\sigma^2_{VA}$ and $\sigma^2_{VV}$. Since the random variables VV and VA are independent, the variance of the AV interval in VT with retrograde conduction, $\sigma^2_{AV}$, is a function of the VA interval variance and the VV interval variance and is calculated as:

$$\sigma^2_{AV} = \sigma^2_{VV} + \sigma^2_{VA}$$

Figure 2:
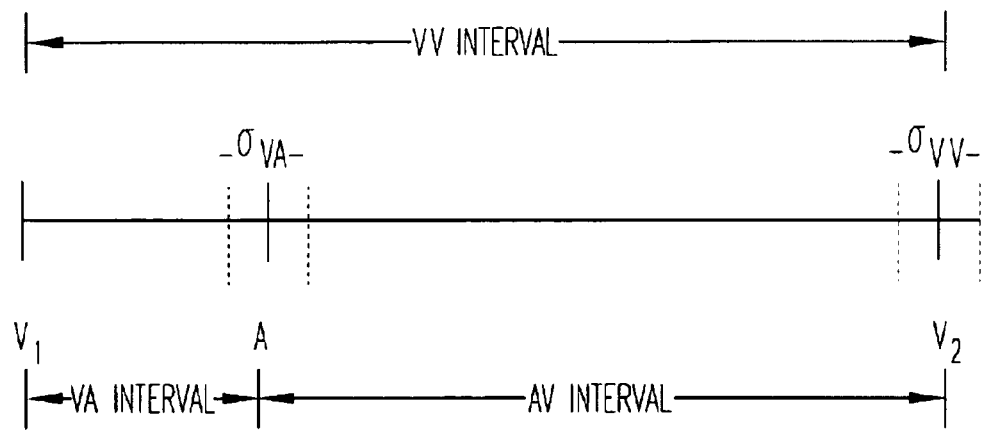
FIG. 2 is a timing diagram of a ventricular rhythm.

This implies the AV variance will be larger than either the VA or VV interval variance during a retrogradely conducting arrhythmia. FIG. 2 shows the timing diagram for this situation.

From this analysis, it can be seen that in an antegrade conduction situation, $\sigma^2_{VA} = \sigma^2_{AA} + \sigma^2_{AV}$, and in a retrograde conduction situation $\sigma^2_{AV} = \sigma^2_{VV} + \sigma^2_{VA}$. In both cases a comparison between $\sigma^2_{AV}$ and $\sigma^2_{VA}$ can be made. In an SVT, $\sigma^2_{VA}$ will always be larger than $\sigma^2_{AV}$ since it is equal to the sum of $\sigma^2_{AV}$ plus another non-zero term. Likewise, in a VT, $\sigma^2_{AV}$ will always be larger than $\sigma^2_{VA}$. The relative magnitudes of these two interval variances is thus evidence of the direction of conduction of the arrhythmia. Therefore, if the AV interval variability is smaller than the VA interval variability, a supraventricular rhythm is likely. Similarly, if the VA interval variability is smaller than the AV interval variability, a retrograde ventricular tachycardia can be predicted to be present.

2. Algorithm Description

An algorithm for detecting specific tachyarrhythmias that incorporates a method for discrimination of 1:1 tachycardias based upon the relative variability of VA and AV intervals will now be described. The algorithm is designed to diagnose the easily identifiable and non-1:1 rhythms using conventional rate-based criteria. If a rhythm does not meet any of these preliminary criteria, it is then considered for 1:1 discrimination using the VA and AV interval variabilities.

The timing differences between atrial and ventricular senses representing depolarization events as detected by a conventional cardiac rhythm management device are used to calculate AA intervals (the time interval between consecutive atrial depolarizations), VV intervals (the time interval between consecutive ventricular depolarizations), AV intervals (the time interval between an atrial depolarization and the next ventricular depolarization—if one exists before the next atrial depolarization), and VA intervals (the time interval between a ventricular depolarization and the next atrial depolarization—if one exists before the next ventricular depolarization). These data can be collected during a sliding data collection time window over a certain number of beats. The first x number of VV intervals are collected together with as many AA, AV, and VA intervals as are included in the time range. A presently preferred value for the number of VV intervals to be contained within the time window is between 8 and 11. The necessary analysis for tachycardia detection as described below is then performed. After that, the next ventricular beat (and thus VV interval) is added to the end of the interval array and the first interval is dropped. At the same time, any AA, AV, or VA intervals that had times equal to or before the dropped VV interval are also dropped and any new values within the next VV interval added. The sliding data collection time window thus acts in a manner similar to a first-in-first-out queue and allows the algorithm to continuously take into account new data.

The first thing an ICD must do for tachyarrhythmia detection is determine if the heart rate in either chamber is unusually fast. For this initial measurement, rate is computed by taking the median or other statistic of the individual cycle lengths for the beats included in the data collection window. A median is preferably used because it is not strongly influenced by possible long or short outliers. Outliers can be present for many reasons including missed or extra triggers and premature complexes which are not part of the driving rhythm. If a fast rate is found in either chamber, then further analysis is performed. If the ventricular rate is above the VF threshold, a VF is diagnosed regardless of what is happening in the rest of the heart. This is the first and most important condition to be checked. When a patient has an ICD implanted, the physician makes an informed decision about the boundary between the rate threshold of ventricular fibrillation and ventricular tachycardia for that patient. Any rhythm with a ventricular rate above the VF threshold is instantly diagnosed as VF to prevent any delay or missed treatment for this lethal condition. An exemplary VF boundary is a 240 ms VV cycle length which corresponds to a ventricular rate of 250 bpm.

Next, the algorithm determines whether the rate in either or both chambers falls in the fast, but non-VF range so as to constitute a tachycardia or is normal, and the rhythm is further classified. Classification is accomplished with four mutually exclusive conditions. The possible combinations are: normal rate in both chambers, fast atrial rate and normal ventricular rate, fast ventricular rate and normal atrial rate, and fast rate in both chambers, where fast rate refers to a rate within a tachycardia range defined for each chamber. If the rate is not fast in either chamber, there is no reason to compute anything further or deliver any therapy. If the rate is fast only in the atrium, then a supraventricular tachycardia can be diagnosed with certainty, and either no therapy or atrial anti-arrhythmic therapy can be given. If only the ventricular rate is fast, a ventricular tachycardia is diagnosed, and ventricular ATP therapy can be delivered. The more difficult situation arises when the rate is fast in both chambers. If this is the case, it is necessary to determine if the rhythm is a 1:1 tachycardia.

A 1:1 tachycardia is defined as when the AA and VV intervals are both within their tachycardia ranges and differ from one another by no more than some specified 1:1 limit value such as a value representing maximum percentage of rate difference or an absolute rate difference. For example, a 1:1 tachycardia may be defined as the situation where the atrial and ventricular rates are in their tachycardia ranges and, additionally, where the rate in the atrium differs by no more than 10 percent of the rate in the ventricles in either direction or where the rate differs by no more than 10 beats per minute in either direction. If the rate in both chambers is fast, but the 1:1 criterion is not satisfied, a dual tachycardia is diagnosed. Since in a dual tachycardia there is independent abnormal activity in both chambers, ventricular tachycardia should be detected, and VT treatment should be administered to avert this potentially dangerous situation. If the 1:1 condition is satisfied, the algorithm advances to the next stage.

After a 1:1 tachycardia condition is detected, a check may next be made that determines whether the rhythm is an atrioventricular nodal reentrant tachycardia (AVNRT). Although technically a supraventricular arrhythmia, AVNRT actually has conduction originating in the AV node and moving upward to the atria and downward to the ventricles simultaneously. Because of this unique propagation pattern, atrial and ventricular depolarizations occur at close to the same time. This contrasts with the situation where one chamber initiates activation in the other chamber sequentially. An AVNRT can therefore be diagnosed when a 1:1 tachycardia condition is present and when either the AV or VA interval is less than a specified AVNRT limit value, irrespective of the AV and VA interval variabilities. An exemplary AVNRT limit value of 80 ms may be used on the premise that propagating AV or VA interval conduction is not likely to be physiologically plausible at times below 80 ms. Thus if either of the AV or VA intervals are below 80 ms, an AVNRT can be diagnosed as a supraventricular arrhythmia with no VT therapy being delivered.

In the next stage, the AV and VA variabilities are calculated. Because outlier values can have such a large effect on a variability measure, such outliers may first be eliminated before computation of the variabilities. As mentioned earlier, outliers can arise from missed or extra triggers, premature complexes in either chamber, sudden changes in morphology, or spurious far-field detections from the other chamber. Outliers can be identified by placing upper and lower bounds around the median value for the AA, AV, VA, and VV intervals contained within a data collection window. If any value in the window occurs outside these bounds, it is not considered in the variability calculation. A more accurate mean value can also be computed from these outlier-adjusted interval arrays. The values for these boundaries can be determined by multiplying the median value by a specified factor. Presently preferred values for factor to be used to determine the upper and lower bounds, respectively, are 1.5 and 0.5.

A standard measure of variability is the variance, which is computed for the AV and VA intervals using the following equation:

$$\text{Variance} = \frac{\sum_{i=1}^{n} (x_i - \mu)^2}{(n-1)}$$

where,
$x_1$ are the interval values
$\mu$ is the mean interval value
n is the total number of intervals Other variability measures are also possible, including: an average deviation calculated as the sum of the absolute value of the difference of each cycle length from the mean divided by the number of cycle lengths in the time window, the difference between the maximum and minimum cycle lengths measured during the time window after the exclusion of outlier values, a difference between an upper percentile value and a lower percentile value of the cycle lengths measured during the time window after the exclusion of outlier values, and a sum of consecutive cycle length differences measured during the time window. Computation for average deviation is almost the same as the variance calculation except that it removes the squared term and replaces it with an absolute value which makes it computationally less demanding. The performance in the algorithm of this metric and the variance variability measure have been determined to be similar and superior to that of the other variability measures. Average deviation is therefore a presently preferred variability measure and can be calculated as:

$$\text{Average Deviation} = \frac{\sum_{i=1}^{n} |x_i - \mu|}{n}$$

where,
$x_1$ are the interval values
$\mu$ is the mean interval value
n is the total number of intervals However the variability measure is computed, a comparison is made between the AV and VA interval varibilities. If AV variability is greater than VA variability, a VT is predicted. Likewise, if the VA variability is greater than the AV variability, an SVT is predicted.

The performance of the algorithm may be further enhanced by taking advantage of the predictive value of the relative magnitudes of the AV and VA intervals during lower rate 1:1 tachycardias. Using this criterion alone, the AV and VA intervals are compared and if the AV interval is smaller than the VA interval, an SVT is diagnosed. If the VA interval is smaller than the AV interval, a VT is diagnosed. The interval-only criterion is not robust physiologically and results in a compromised sensitivity to VT when used over a wide range of VV cycle lengths. It works better at longer VV cycle lengths, however, because in that case, only one of the two intervals (AV or VA) will have a duration that can be expected to plausibly represent conduction through the AV node. In an SVT, the AV interval represents the conduction time of the electrical impulse from the atrium to the ventricles. The VA interval is merely the remainder of the cycle length (the subtraction of the AV interval from the VV interval) and is thus highly rate dependent. Slower rates will produce longer VA intervals, and faster rates will produce shorter VA intervals. For fast tachycardias, both the AV interval size and the VA interval size can be in normal expected ranges for conduction. There is a point, however, at which the rate of an SVT extends the VA interval to durations no longer realistic for ventriculoatrial conduction. Here, the diagnosis of SVT is straightforward because a VT with 1:1 retrograde conduction without AV block is impossible at VA intervals that large. The same principle works in reverse for VTs. So at long cycle lengths, or slower rates, the interval only method is accurate.

The benefits of the interval-only method can be combined with the variability method by diagnosing slower 1:1 tachycardias using the interval criterion and faster 1:1 tachycardias using the variability criterion. To distinguish fast and slow tachycardias for this purpose, a parameter called the ratebreak threshold is compared with the VV interval. All 1:1 tachycardias with a VV cycle length greater than this threshold are diagnosed using the relative magnitudes of the AV and VA intervals. All 1:1 tachycardias with a VV cycle length less than this threshold are diagnosed using the relative variabilities of the AV and VA intervals. A presently preferred value for the ratebreak threshold parameter is 340 milliseconds.

When a patient has first degree AV nodal block, the function of the AV node is impaired and the AV conduction time is much longer than normal. Sometimes AV block can develop suddenly during a tachycardia, but often it is present and can be diagnosed during normal sinus rhythm. AV block is diagnosed by a simple measurement of the AV interval during normal sinus rhythm. If the AV interval during normal sinus rhythm is greater than 200 milliseconds, the patient is said to have first degree AV block. The implications of AV block to a discrimination algorithm which uses interval information for diagnosis are substantial. Patients with first degree AV nodal block have an abnormally long AV interval during SVTs which creates an unusually short VA interval for the given rate. An algorithm which uses interval measurements is confounded by patients with AV block since these patients present AV and VA intervals which are far from normal.

With the present algorithm, if the ventricular rate is faster than the ratebreak threshold so that diagnosis is made on the basis of relative AV and VA interval variability and not on the basis of the magnitudes of those intervals, no problem is presented by patients with first degree AV block. If the VV interval is greater than the ratebreak threshold, however, patients with first degree block may be misdiagnosed without a further modification to the algorithm. Although AV block can be intermittent and hence undiagnosed, and can develop over time after implantation, a physician will generally know which patients have chronic AV block and can easily enter that information into a device when programming the other required fields. In such patients identified to have first degree AV block, the modified algorithm does not employ relative magnitudes of the AV and VA intervals to diagnose 1:1 tachycardias and uses only relative AV and VA interval variability instead. An additional criterion, however, may also be used for patients with first degree AV block: a VT is detected if a baseline measured AV conduction time in the patient is less than a specified AV block limit value and the AV interval during a tachycardial is greater than a specified tachycardia AV limit value. Exemplary values for the specified AV block limit value and the specified tachycardia limit value are 270 and 300 milliseconds, respectively. A common distinguishing feature of VT patients with first degree AV block is that they have a normal AV interval of greater than 200 milliseconds and a tachycardia AV interval that may increase to greater than 300 milliseconds. It is unlikely for a patient with first degree AV block to have an AV interval increase by as much as 30 milliseconds during an SVT. If a patient with first degree AV block has a baseline measured AV interval of less than 270 ms which increases to more than 300 ms during a tachycardia, a ventricular tachycardia can be confidently diagnosed. Otherwise, the diagnosis is made by AV and VA interval variability alone without using AV and VA interval magnitudes regardless of the cycle length.

Further modifications may be made to implementation details of the algorithm in order to improve its performance. For example, the algorithm may make a rhythm diagnosis after looking at just one window, or it may require diagnosis information over several shifts of the window before making the diagnosis. In a presently preferred embodiment, the time window is shifted a specified number of times before making a decision. All of the diagnoses from each shift of the window are then required to be identical before a final decision is made. If there is any disagreement or if a window within this time is not satisfied, the algorithm continues until an agreement is reached over consecutive windows shifted the specified number of times, or until a sustained high rate timer expires at which time VT therapy is given to ensure patient safety. A presently preferred value for the specified number of required window shifts is four. Also, the algorithm may require all individual beats within the window to demonstrate the cycle length required, or may require some fraction of them to do so. A presently preferred embodiment is to require 100% of the beats in a window to demonstrate the cycle length required for a diagnosis.

The algorithm may be further modified by adding a criterion to eliminate the confusion that can occur during onset (or spontaneous conversion if relevant) of an arrhythmia. If AV and VA variability is being measured to diagnose arrhythmias and some of the beats in the window are supraventricular and non-arrhythmogenic (such as fast sinus rhythm) and some of them due to a ventricular arrhythmia, their different characteristics will increase the variability measure and produce confused results. The window should ideally, of course, contain only cycles of the arrhythmia of interest. The most common reason for containing other cycles is that the window has captured the onset or termination of the arrhythmia along with some pre-arrhythmia or post-arrhythmia data. To avoid this, the algorithm may require that both the first and last cycles in the window be in the tachycardia rate range. This is further emphasized as the window is shifted because the first and last cycles must be at tachycardia rates for all shifts of the window.

3. Hardware Platform

In the description that follows, a microprocessor-based cardiac rhythm management device will be referred to as incorporating the system and method that is the present invention. In the embodiment to be described, the invention is implemented with a control unit made up of a microprocessor executing programmed instructions in memory. It should be appreciated, however, that certain functions of a cardiac rhythm management device could be controlled by custom logic circuitry either in addition to or instead of a programmed microprocessor. The term "controller" as used herein should therefore be taken to encompass either custom circuitry (i.e., dedicated hardware) or a microprocessor executing programmed instructions contained in a processor-readable storage medium along with associated circuit elements.

Figure 3:
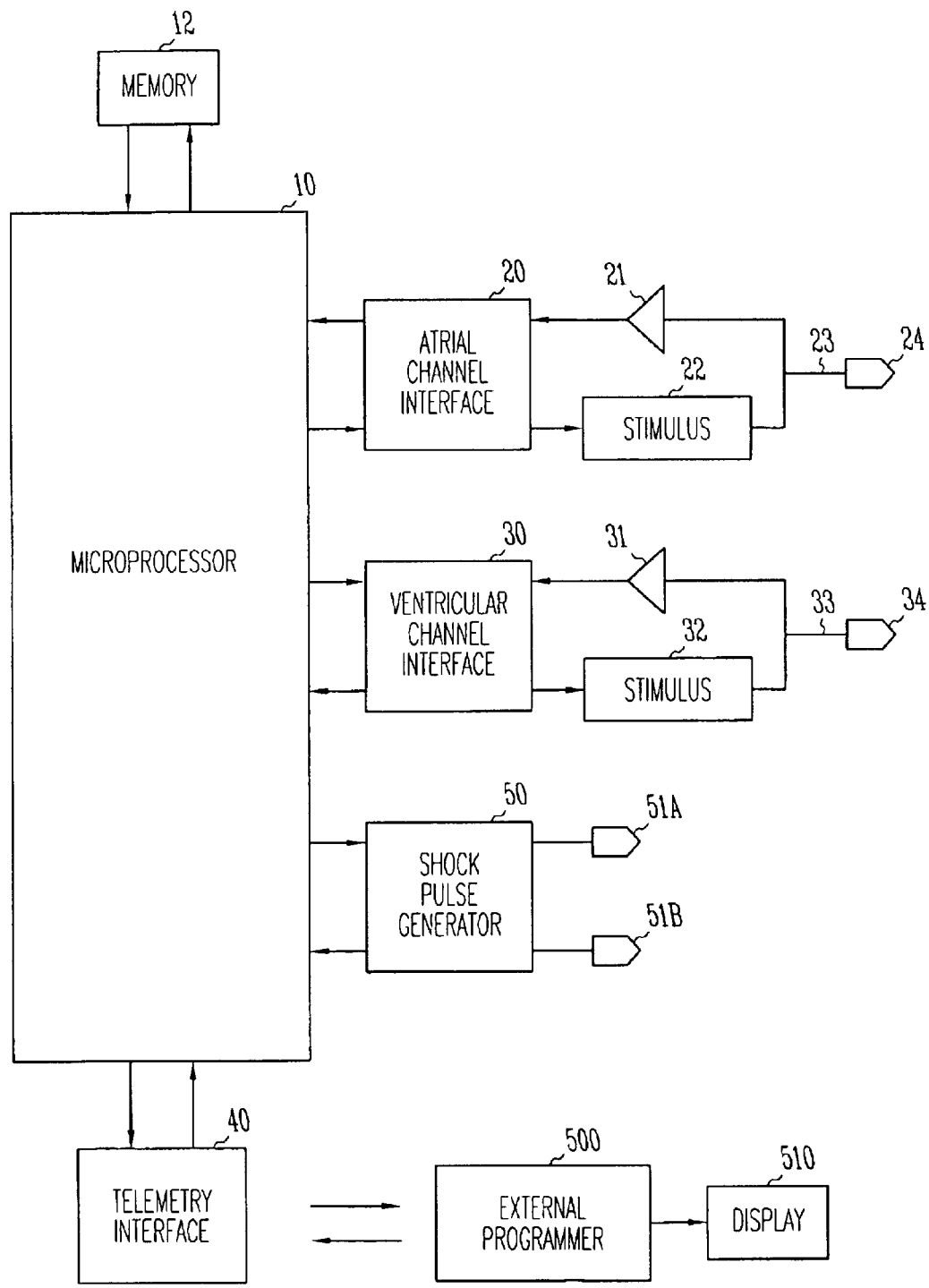
FIG. 3 is a block diagram of a cardiac rhythm management device with ATP and cardioversion/defibrillation capability.

Implantable cardiac rhythm management devices, such as pacemakers and ICD's, are electronic devices that are implanted subcutaneously on a patient's chest with leads threaded intravenously into the heart to connect the device to electrodes used for sensing electrical activity and for electrical stimulation of the heart. FIG. 3 is a system diagram of a microprocessor-based cardiac rhythm management device with the capability of delivering cardioversion/defibrillation shocks as well as antitachycardia pacing (ATP) therapy. The device may also be configured to deliver conventional (e.g., bradycardia) pacing as well. The controller 10 of the pacemaker is a microprocessor that communicates with a memory 12 via a bidirectional data bus. The memory 12 typically comprises a ROM (read-only memory) for program storage and a RAM (random-access memory) for data storage. The pacemaker has atrial and ventricular sensing/pacing channels that respectively include electrodes 24 and 34, leads 23 and 33, sensing amplifiers 21 and 31, pulse generators 22 and 32, and ventricular channel interfaces 20 and 30. Incorporated into each sensing/pacing channel is thus a pacing channel made up of the pulse generator connected to the electrode and a sensing channel made up of the sense amplifier connected to the electrode. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces communicate bidirectionally with microprocessor 10 and include analog-to-digital converters for digitizing sensing signal inputs from the sense amplifiers and registers that can be written to by the microprocessor in order to adjust the gain and threshold values for the sensing amplifiers, output pacing pulses, and change the pacing pulse amplitude and/or duration. A telemetry interface 40 is also provided for communicating with an external programmer 500 that has an associated display 510.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when a sense signal (i.e., a voltage sensed by an electrode representing cardiac electrical activity, sometimes called an electrogram signal) generated by a particular channel exceeds a specified intrinsic detection threshold. A chamber sense may be either an atrial sense or a ventricular sense depending on whether it occurs in the atrial or ventricular sensing channel. Pacing algorithms used in particular pacing modes employ such senses to trigger or inhibit pacing. By measuring the interval between successive chamber senses, the controller is also able to detect arrhythmias in the chamber based upon rate.

4. Exemplary Algorithm Implementation

Figure 4:
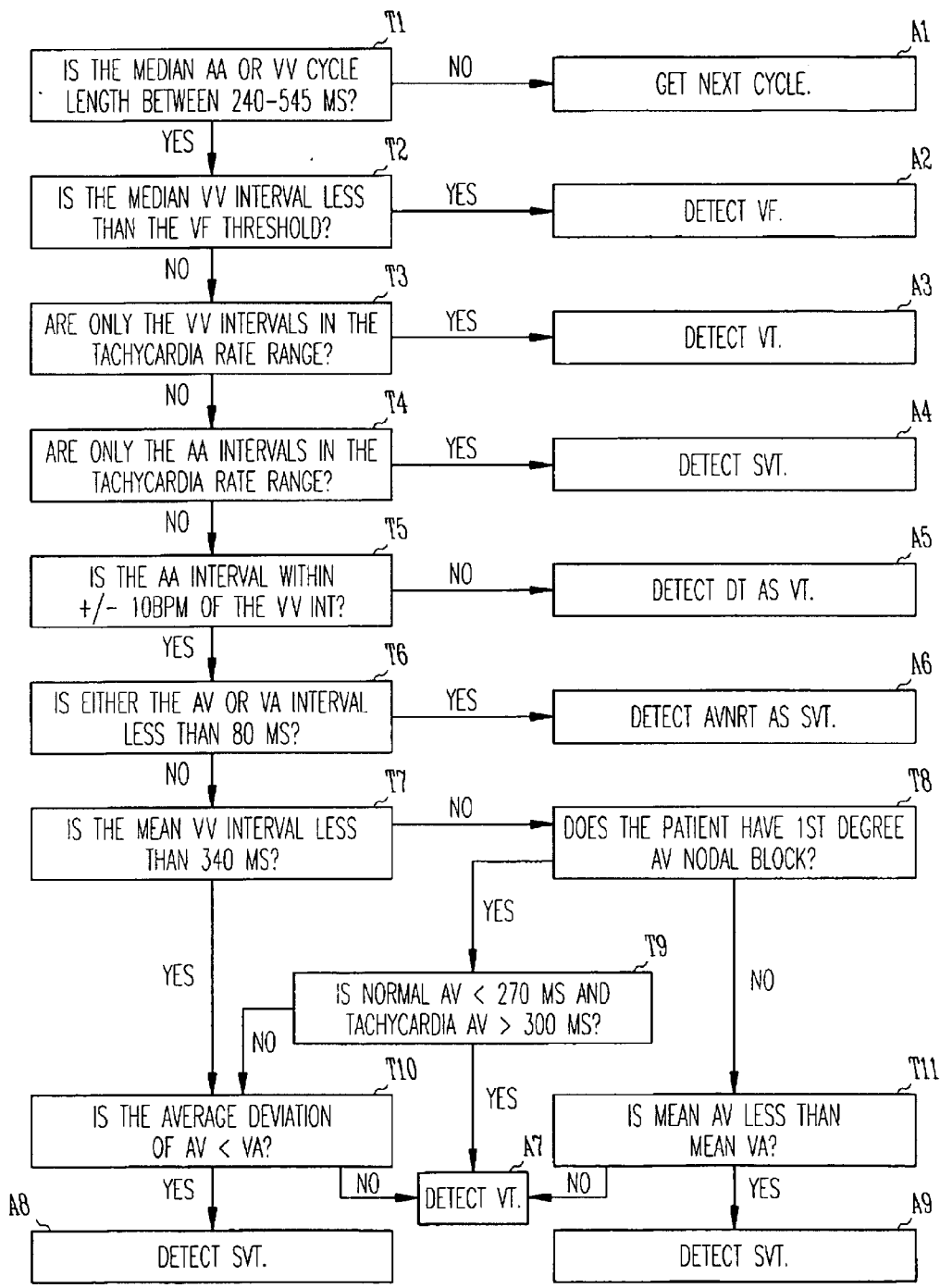
FIG. 4 is a flowchart of an exemplary implementation of the invention.

FIG. 4 is a flowchart illustrating one particular embodiment of the SVT/VT discrimination algorithm as it could be implemented in the device of FIG. 3 by programming of the controller. The order of steps taken in the algorithm is largely organized by the criticality of the rhythm suspected. All of the metrics used are median or mean values computed over a single window of cycles. First, the atrial and ventricular rates are measured at step T1 to determine if either is in the fast tachycardia zone. If neither of these rates is fast, nothing further needs to be computed and the next cycle is obtained at step A1. If either chamber demonstrates a fast rate, the next step is to determine whether ventricular fibrillation (VF) is occurring. The condition used to test this is a ventricular cycle length threshold. If the median ventricular cycle length is smaller than the VF threshold at step T2, VF is detected at step A2. If VF is not detected and the only chamber demonstrating a fast rate is the ventricular chamber as determined at step T3, ventricular tachycardia (VT) is detected at step A3. If the ventricular chamber does not have a fast rate but the atrial chamber does as determined at step T4, supraventricular tachycardia (SVT) is detected at step A4.

If none of the conditions have been satisfied thus far, a rhythm with a fast rate in both chambers has been identified. The next step is to determine if this rhythm is one-to-one (1:1). If the atrial rate does not differ by more than 10 beats per minute (bpm) in either direction of the ventricular rate at step T5, a 1:1 tachycardia is present. Otherwise, dual tachycardia (DT) is diagnosed at step A5 and VT therapy is recommended. If the rhythm is 1:1, a subset of SVTs, atrioventricular nodal reentrant tachycardias (AVNRT), can be diagnosed fairly easily by checking if either the AV or VA interval is less than 80 ms at step T6. If so, SVT is diagnosed at step A6.

If the rhythm is not an AVNRT, the mean VV interval is compared to a threshold of 340 ms at step T7. If the VV interval is less than 340 ms, the average deviation of the AV and VA intervals is measured. If the average deviation of the AV interval is less than the average deviation of the VA interval at step T10, SVT is diagnosed at step A8. Otherwise, VT is diagnosed at step A7. If, however, the VV interval is greater than 340 ms at step T7, the algorithm checks the normal AV interval size to determine if the patient has first degree AV nodal block at step T8. If the patient does not have AV block and the mean AV interval is less than the mean VA interval at step T11, SVT is detected at step A9. If the patient does not have AV block and the mean AV interval is greater than the mean VA interval, VT is detected at step A7. If the patient does have AV block and the normal AV interval is less than 270 ms but the tachycardia interval is greater than 300 ms at step T9, VT is detected at step A7. This condition is imposed to safely and easily address some of the VT cases without having to compute average deviation. If the patient has AV block but the condition is not met at step T9, the patient is diagnosed by average deviation by determining whether the average deviation of the AV interval is less than the average deviation of the VA interval at step T10. If it is, SVT is detected at step A8. Otherwise, VT is detected at step A7.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   an atrial sensing channel for detecting atrial senses corresponding to atrial depolarizations;
   a ventricular sensing channel for detecting ventricular senses corresponding to ventricular depolarizations;
   a controller for detecting arrhythmias based upon the atrial and ventricular senses detected in the sensing channels, wherein the controller is programmed to:

compute an AA interval corresponding to a cycle length between consecutive atrial senses, a VV interval corresponding to a cycle length between consecutive ventricular senses, an AV interval corresponding to a cycle length between an atrial sense and a next occurring ventricular sense with no intervening atrial sense, and a VA interval corresponding to a cycle length between a ventricular sense and a next occurring atrial sense with no intervening ventricular sense;

compute variabilities for both the VA and AV intervals based upon their measured individual cycle lengths during a specified time window;

detect a supraventricular tachycardia (SVT) when: (a) the AA interval is within a tachycardia range defined as below an SVT threshold and (b) the VV interval is within normal limits;

detect a ventricular fibrillation (VF) when the VV interval is below a VF threshold;

detect a ventricular tachycardia (VT) when: (a) the VV interval is within a tachycardia range defined as above the VF threshold but below a VT threshold and (b) the AA interval is either within normal limits or differs from the VV interval by more than a specified dual tachycardia limit value; and, if a 1:1 tachycardia condition is present, defined as when the AA and VV intervals are both within their tachycardia ranges and differ from one another by no more than a specified 1:1 limit value, discriminate between a supraventricular tachycardia and a ventricular tachycardia based upon a relative variability of the VA and AV intervals.

2. The device of claim 1 wherein the AA, VV, VA, and AV intervals are statistics computed from individual cycle lengths measured during a data collection time window.

3. The device of claim 2 wherein the AA, VV, VA, and AV intervals are medians of individual cycle lengths measured during the data collection time window.

4. The device of claim 1 wherein the controller is further programmed to detect an atrioventricular nodal reentrant tachycardia (AVNRT) when a 1:1 tachycardia condition is present and when either the AV or VA interval is less than a specified AVNRT limit value, irrespective of the AV and VA interval variabilities.

5. The device of claim 1 wherein the controller is further programmed to discriminate between a supraventricular tachycardia and a ventricular tachycardia when a 1:1 tachycardia condition is present by:

detecting a supraventricular tachycardia if the VA interval variability exceeds the AV interval variability;

detecting a ventricular tachycardia if the AV interval variability exceeds the VA interval variability.

6. The device of claim 1 wherein the controller is further programmed to discriminate between a supraventricular tachycardia and a ventricular tachycardia when a 1:1 tachycardia condition is present and the VV interval is more than a specified ratebreak threshold value, irrespective of the AV and VA interval variabilities, by:

detecting a supraventricular tachycardia if the VA interval exceeds the AV interval; and, detecting a ventricular tachycardia if the AV interval exceeds the VA interval.

7. The device of claim 6 wherein the controller is further programmed to discriminate between a supraventricular tachycardia and a ventricular tachycardia when a 1:1 tachycardia condition is present based upon the relative variability of the VA and AV intervals, irrespective of whether the VV interval is more than the specified ratebreak threshold value, when a patient in whom the device is operating has an AV nodal block.

8. The device of claim 7 wherein the controller is further programmed to discriminate between a supraventricular tachycardia and a ventricular tachycardia when a 1:1 tachycardia condition is present and the patient in whom the device is operating has an AV nodal block, irrespective of the relative variability of the VA and AV intervals, by detecting a ventricular tachycardia if a measured AV conduction time in the patient is less than a specified AV block limit value and the AV interval is greater than a specified tachycardia AV limit value.

9. The device of claim 8 wherein the specified AV block limit value is 270 milliseconds and the specified tachycardia limit value is 300 milliseconds.

10. The device of claim 1 wherein the controller is further programmed to compute each of the AV and VA interval variabilities as a measure selected from a group consisting of: a variance of the cycle lengths measured during the specified time window, a difference between the maximum and minimum cycle lengths measured during the specified time window after the exclusion of outlier values, a difference between an upper percentile value and a lower percentile value of the cycle lengths measured during the specified time window after the exclusion of outlier values, and an average deviation that is calculated as the sum of the absolute value of the difference of each cycle length from the mean divided by the number of cycle lengths in the time window.

11. A method for operating a cardiac rhythm management device, comprising:

detecting atrial senses corresponding to atrial depolarizations;

detecting ventricular senses corresponding to ventricular depolarizations;

computing an AA interval corresponding to a cycle length between consecutive atrial senses, a VV interval corresponding to a cycle length between consecutive ventricular senses, an AV interval corresponding to a cycle length between an atrial sense and a next occurring ventricular sense with no intervening atrial sense, and a VA interval corresponding to a cycle length between a ventricular sense and a next occurring atrial sense with no intervening ventricular sense;

computing variabilities for both the VA and AV intervals based upon their measured individual cycle lengths during a specified time window;

detecting a supraventricular tachycardia (SVT) when: (a) the AA interval is within a tachycardia range defined as below an SVT threshold and (b) the VV interval is within normal limits;

detecting a ventricular fibrillation (VF) when the VV interval is below a VF threshold;

detecting a ventricular tachycardia (VT) when: (a) the VV interval is within a tachycardia range defined as above the VF threshold but below a VT threshold and (b) the AA interval is either within normal limits or differs from the VV interval by more than a specified dual tachycardia limit value; and, if a 1:1 tachycardia condition is present, defined as when the AA and VV intervals are both within their tachycardia ranges and differ from one another by no more than a specified 1:1 limit value, discriminating between a supraventricular tachycardia and a ventricular tachycardia based upon a relative variability of the VA and AV intervals.

12. The method of claim 11 wherein the AA, VV, VA, and AV intervals are statistics computed from individual cycle lengths measured during a data collection time window.

13. The method of claim 12 wherein the AA, VV, VA, and AV intervals are medians of individual cycle lengths measured during the data collection time window.

14. The method of claim 11 further comprising detecting an atrioventricular nodal reentrant tachycardia (AVNRT) when a 1:1 tachycardia condition is present and when either the AV or VA interval is less than a specified AVNRT limit value, irrespective of the AV and VA interval variabilities.

15. The method of claim 11 further comprising discriminating between a supraventricular tachycardia and a ventricular tachycardia when a 1:1 tachycardia condition is present by:

detecting a supraventricular tachycardia if the VA interval variability exceeds the AV interval variability;

detecting a ventricular tachycardia if the AV interval variability exceeds the VA interval variability.

16. The method of claim 11 further comprising discriminating between a supraventricular tachycardia and a ventricular tachycardia when a 1:1 tachycardia condition is present and the VV interval is more than a specified ratebreak threshold value, irrespective of the AV and VA interval variabilities, by:

detecting a supraventricular tachycardia if the VA interval exceeds the AV interval; and, detecting a ventricular tachycardia if the AV interval exceeds the VA interval.

17. The method of claim 16 further comprising discriminating between a supraventricular tachycardia and a ventricular tachycardia when a 1:1 tachycardia condition is present based upon the relative variability of the VA and AV intervals, irrespective of whether the VV interval is more than the specified ratebreak threshold value, when a patient in whom the device is operating has an AV nodal block.

18. The method of claim 17 further comprising discriminating between a supraventricular tachycardia and a ventricular tachycardia when a 1:1 tachycardia condition is present and the patient in whom the device is operating has an AV nodal block, irrespective of the relative variability of the VA and AV intervals, by detecting a ventricular tachycardia if a measured AV conduction time in the patient is less than a specified AV block limit value and the AV interval is greater than a specified tachycardia AV limit value.

19. The method of claim 18 wherein the specified AV block limit value is 270 milliseconds and the specified tachycardia limit value is 300 milliseconds.

20. The method of claim 11 wherein the AV and VA interval variabilities are computed as variances of their individual cycle lengths measured during the specified time window.

21. The method of claim 11 wherein the AV and VA interval variabilities are each computed as a difference between the maximum and minimum cycle lengths measured during the specified time window after the exclusion of outlier values.

22. The method of claim 11 wherein the AV and VA interval variabilities are each computed as a difference between an upper percentile value and a lower percentile value of the cycle lengths measured during the specified time window after the exclusion of outlier values.

23. The method of claim 11 wherein the AV and VA interval variabilities are each computed as an average deviation that is calculated as the sum of the absolute value of the difference of each cycle length from the mean divided by the number of cycle lengths in the time window.

24. The method of claim 11 wherein the AV and VA interval variabilities are each computed as a sum of consecutive cycle length differences measured during the time window.

25. A cardiac rhythm management device configured to detect atrial and ventricular beats and further configured to discriminate between a supraventricular tachycardia and a ventricular tachycardia by comparing a variability of an AV interval, defined as the interval between an atrial beat and a next occurring ventricular beat with no intervening atrial beat, with a variability of a VA interval, defined as the interval between a ventricular b eat and a next occurring atrial beat with no intervening ventricular beat.

26. A method for discriminating between a supraventricular tachycardia and a ventricular tachycardia, comprising comparing a variability of an AV interval, defined as the interval between an atrial beat and a next occurring ventricular beat with no intervening atrial beat, with a variability of a VA interval, defined as the interval between a ventricular beat and a next occurring atrial beat with no intervening ventricular beat.

* * * * *

UNITED STATES PATENT AND TRADEMARK OFFICE
CERTIFICATE OF CORRECTION

PATENT NO. : 6,748,269 B2
DATED : June 8, 2004
INVENTOR(S) : Thompson et al.

It is certified that error appears in the above-identified patent and that said Letters Patent is hereby corrected as shown below:

<u>Title page,</u>
Item [75], Inventors, delete "White Bear Lake" and insert -- Circle Pines --, therefor.

<u>Column 16,</u>
Line 35, delete "b eat" and insert -- beat --, therefor.

Signed and Sealed this

Fifteenth Day of November, 2005

JON W. DUDAS
*Director of the United States Patent and Trademark Office*